(12) United States Patent
Apffel

(10) Patent No.: US 6,284,115 B1
(45) Date of Patent: Sep. 4, 2001

(54) IN-LINE FLOW THROUGH MICRO-DIALYSIS APPARATUS AND METHOD FOR HIGH PERFORMANCE LIQUID PHASE SEPARATIONS

(75) Inventor: James A. Apffel, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/399,971

(22) Filed: Sep. 21, 1999

(51) Int. Cl.$^7$ .................................................. B01D 61/42
(52) U.S. Cl. ............................................ 204/518; 204/627
(58) Field of Search .................................. 204/627, 518, 204/541

(56) References Cited

U.S. PATENT DOCUMENTS

| 3,674,669 | 7/1972 | Tuwiner | 2204/180 P |
| 4,146,455 | 3/1979 | McRae | 204/180 P |
| 4,180,451 | 12/1979 | McRae | 204/301 |

(List continued on next page.)

FOREIGN PATENT DOCUMENTS

| 2340362 | 2/1974 | (DE) . |
| 3337668 | 5/1985 | (DE) . |
| 5-271269 | * 10/1996 | (JP) . |

OTHER PUBLICATIONS

Bier, Milan et al., "Separation of Lens culinaris Hemagglutinin by Forced Flow Electrophoresis", Separation Science and Technology, vol. 25, Nos. 9 & 10, 1990, pp. 997–1005 No month given.

Gobel, Ulf et al., "Quantitative Electroelution of Oligonucleotides and Large DNA Fragments from Gels and Purification by Electrodialysis", Journal of Biochemical and Biophysical Methods, vol. 14, 1987, pp. 245–260 No month given.

Lada, Mark W. et al., "On–Line Interface Between Microdialysis and Capillary Zone Electrophoresis", Analytica Chimica Acta, vol. 307, 1995, pp. 217–225 No month given.

(List continued on next page.)

Primary Examiner—Kathryn Gorgos
Assistant Examiner—Thomas H. Parsons

(57) ABSTRACT

Apparatus for in-line flow-through sample treatment includes a sample channel that has a sample inlet and a sample outlet and is defined in part by inner surfaces of walls of a solid material and in part by an inner surface of a first membrane, and a first flushing channel that has an inlet port and an outlet port and is defined in part by inner surfaces of walls of a solid material and in part by an outer surface of the first membrane. An electric field is applied across the first membrane in liquids carried within the sample channel and the first flushing channel. The analytical stream flows from an upstream liquid analysis device, such as a liquid chromatographic column, into the sample inlet and through the sample channel and out from the sample outlet, and a flushing liquid flows into the inlet port and through the flushing channel and out from the outlet port. Charged particles (such as ions of inorganic salts) in the analytical stream move in a direction generally away from or toward the membrane. Particles (including solvent molecules) sufficiently small to pass through the membrane move across the membrane from the sample channel to the flushing channel, in which they are carried away by the flushing liquid. Thus, a rapid enrichment of sample analytes in the analytical results.

17 Claims, 6 Drawing Sheets

U.S. PATENT DOCUMENTS

| | | | |
|---|---|---|---|
| 4,441,978 | 4/1984 | Jain | 204/301 |
| 4,576,696 | 3/1986 | Oertli | 204/182.6 |
| 4,614,576 | 9/1986 | Goldstein | 204/299 R |
| 5,055,399 | 10/1991 | Snedecor et al. | 435/68.1 |
| 5,082,548 | 1/1992 | Faupel et al. | 204/299 R |
| 5,336,387 | 8/1994 | Egen et al. | 204/301 |
| 5,437,774 * | 8/1995 | Laustsen | 204/182.3 |
| 5,480,526 | 1/1996 | Liao et al. | 204/182.8 |

OTHER PUBLICATIONS

Huang, Ting–Chia and Wang, Jau–Kai, "Preferential Transport of Cupric and Ferric Ions Through Ion Exchange Membranes with Electrodialysis in the Presence of Citric Acid", Chemical Engineering Communications, vol. 122, 1993, pp. 213–225 No month given.

Bowen, Richard W., "Electrically Driven Membrane Processes", Chromatographic and Membrane Processes in Biotechnology, vol. 204, 1991, pp. 207–221 No month given.

Takahashi, Katsuroku et al., "Multi State Electrodialysis for Separation of Two Metal Ion Species", Journal of Chemical Engineering of Japan, vol. 28, No. 2, 1995, pp. 154–158 No month given.

Debets, A.J.J. et al., "Theoretical Models for ElectrodialyticSample Treatment in Trace Analysis by Liquid Chromatography", Chromatographia, vol. 39, No. 7/8, 1994, pp. 460–468 No month given.

Debets, A.J.J. et al., "Electrodialytic Sample Treatment Coupled On–Line with Column Liquid Chromatography for the Determination of Basic and Acidic Comounds in Environmental Samples", Journal of Chromatography, vol. 600, 1992, pp. 163–173 No month given.

Debets, A.J.J. et al., "Electrodialytic Sample Treatment Coupled On–Line with High–Performance Liquid Chromatography", Chromatographia, vol. 30, No. 7/8, Oct. 1990, pp. 361–366.

Jacobs, Enno and Clad, Andreas, "Electroelution of Fixed and Stained Membrane Proteins from Preparative Sodium Dodecyl Sulfate–Polyacrylamide Gels into a MembraneTrap", Analytical Biochemistry, vol. 154, 1986, pp. 583–589 No month given.

Apffel, Alex et al., "Enhanced sensitivity for peptide mapping with electrospray liquid chromatography–mass spectrometry in the presence of signal suppression due to trifluoroacetic acid–containing mobile phases", Journal of Chromatography A, vol. 712, 1995, pp. 177–190 No month given.

http://www.sialomed.com/electroe.htm, "Electroelutor", Amika Corp., printed Aug. 14, 1998.

http://www.sialomed.com/electrod.htm, "Electrodialysis", Amika Corp., printed Aug. 14, 1998.

http://www.sialomed.com/electro.htm, "Electroconcentrator", Sialomed Corp., printed Aug. 14, 1998.

* cited by examiner

IN-LINE FLOW THROUGH MICRO-DIALYSIS APPARATUS AND METHOD FOR HIGH PERFORMANCE LIQUID PHASE SEPARATIONS

BACKGROUND OF THE INVENTION

1. Field of the Invention

This invention relates to enrichment of analytes in liquid sample analysis.

2. Description of the Related Art

In a range of multidimensional analytical techniques, the presence of non-analyte, matrix-related substances required for one analytical dimension often interfere with another dimension, and in these circumstances it is desirable to remove non-analytes from the analytical stream flowing from an upstream analytical dimension before the stream is introduced to a subsequent downstream analytical dimension in the scheme. In particular, for example, for liquid phase based separation techniques, it is desirable to remove non-analyte(s) from the analytical stream in an on-line flow-through manner without compromising the analytical procedure.

In liquid phase separation techniques, such as High Performance Liquid Chromagraphy ("HPLC"), mixtures are separated from each other spatially, volumetrically and temporally in a flowing stream. The resolution of such a system is based on the separation between the mean of the concentration profile for two peaks relative to the standard deviation of the concentration profile of each of the peaks. The separation process itself introduces an increase in the variance of the concentration profile. However, further increase in the variance (also known as band broadening, peak broadening or dispersion) is introduced as the analyte peaks pass through extra-column "dead-volume" such as connecting tubes, detector flow cells and mixing chamber. Particularly for modern miniaturized chromatography systems, this extra dispersion can be unacceptable and steps are taken to minimize it.

In mass spectrometry ("MS") where electrospray ionization is employed, introduction of non-volatile salts into the electrospray ion source leads to diminished performance. Accordingly, contamination of a sample stream from a liquid chromatography ("LC") column by non-volatile salts effectively precludes the use of ion exchange chromatography as a separation technique in analytical systems in which liquid chromatography is coupled with mass spectrometry ("LC/MS").

Electrodialytic treatment may be employed for isolation and enrichment of compounds from complex solutions. Publications of interest with respect to sample treatment using electrodialysis or electrofiltration include: A. J. J. Debets et al. (1992), *Journal of Chromatography*, Vol. 600, pp. 163–173; A. J. J. Debets, et al. (1990), *Chromatographia*, Vol. 30, No. 7/8, pp. 361–366; A. J. J. Debets, et al. (1994), *Chromatographia*, Vol. 39, No. 7/8, pp. 460–468; M. W. Lada, et al. (1995), *Analytica Chemica Acta*, Vol. 307, pp. 217–225; E. Jacobs, et al. (1986), *Analytical Biochemistry*, Vol. 154, pp. 583–589; W. R. Bowen (1991), "Electrically Driven Membrane Process", in *Chromatographic and Membrane Processes in Biotechnology*, C. A. Costa and J. S. Cabral, eds., Kluwer Academic Publishers, Dordrecht, Netherlands, pp. 207 to 221 (review); K. Takahashi et al. (1995), *Journal of Chemical Engineering of Japan*, Vol. 28, No. 2, pp. 154–158; T.-C. Huang et al. (1993), *Chemical Engineering Communications*, Vol. 122, pp. 213–225; U. Göbel et al. (1987), *Journal of Biochemical and Biophysical Methods*, Vol. 14, pp. 245–260; M. Bier et al. (1990), *Separation Science and Technology*, Vol. 25, Nos. 9/10, pp. 997–1005; E. Sommerfeld et al., German patent publication 2,340,362; N. B. Egen, et al. U.S. Pat No. 5,336,387; J. -I. Liao, et al. U.S. Pat. No. 5,480,526; S. M. Jain, U.S. Pat. No. 4,441,978; R. Oertli, U.S. Pat. No. 4,576,696; J. M. Goldstein, U.S. Pat. No. 4,614,576; W. A. McRae, U.S. Pat. No. 4,146,455 and 4,180,451; and S. B. Tuwiner, U.S. Pat. No. 3,674,669.

Additional publications and patents of interest include U.S. Pat. No. 5,082,548 and U.S. Pat. No. 5,055,399; and N. Hese et al., German patent publication 3,337,668.

All articles, references, standards, patents, patent applications and the like referred to herein are hereby incorporated herein by reference in their entirety.

SUMMARY OF THE INVENTION

The degree to which components below a molecular weight cutoff are removed from a solution by a dialysis system is based on the mixing and the residence time in the apparatus. Micro-dialysis can be employed in the stream downstream from an LC column. In an in-line, post-column micro-dialysis system, complete removal of low molecular weight salts requires a long residence time in the micro-dialysis zone, resulting in excessive dispersion. According to the invention, an electric field is applied to the micro-dialysis zone, providing for an accelerated movement of smaller charged molecules (such as non-volatile salts) across the dialysis membrane and resulting in a reduction in the residence time in dialysis. Samples can be enriched for subsequent analysis without unacceptable loss of chromatographic fidelity, and non-volatile salts can be removed from the analytical stream without introducing excessive dilution or chromatographic band broadening.

Accordingly, the invention provides methods and an apparatus for sample treatment by in-line flow-through electromicro-dialysis.

In one general aspect, the invention features an apparatus for in-line flow-through sample treatment, including a sample channel having a sample inlet and a sample outlet and being defined in part by inner surfaces of walls of a solid material and in part by an inner surface of a first membrane, and a first flushing channel having an inlet port and an outlet port and being defined in part by inner surfaces of walls of a solid material and in part by an outer surface of the first membrane, and means for applying an electric field across the first membrane in liquids carried within the sample channel and the first flushing channel.

The analytical stream flows from an upstream liquid analysis device, such as a liquid chromatographic column, into the sample inlet and through the sample channel and out from the sample outlet, and a flushing liquid flows into the inlet port and through the flushing channel and out from the outlet port. The electric field is applied, causing charged particles (such as ions of inorganic salts) in the analytical stream to move in a direction, depending upon their respective charges, generally away from or toward the membrane. Particles (including solvent molecules) sufficiently small to pass through the membrane move across the membrane from the sample channel to the flushing channel, in which they are carried away by the flushing liquid. Thus, as the analytical stream flows through the dialysis zone smaller particles are removed from the analytical stream, and smaller charged particles are removed particularly rapidly under force of the electric field, resulting in a rapid enrichment of sample analytes in the analytical stream.

In some embodiments, the sample channel is further defined in part by an inner surface of a second membrane, and the apparatus further includes a second flushing channel having an inlet port and an outlet port and being defined in part by inner surfaces of walls of a solid material and in part by an outer surface of the second membrane; and the means for applying an electric field includes means for applying the electrical field across both the first membrane and the second membrane in liquids carried within the sample channel and the flushing channels. In such embodiments, application of the electrical field results in movement of particles having one charge polarity toward the first membrane and in movement of particles having opposite charge polarity toward the second membrane.

The membrane (or, where two membranes are employed, each of them) has a molecular size-selective permeability selected according to the sizes of the particular molecules whose removal is desired, as is well understood in the dialysis art. In some embodiments, conventional dialysis membrane material suitable for electrodialysis is employed, having a nominal molecular weight cut-off, for example, about 30,000 daltons, 10,000 daltons, 5,000 daltons, 1,000 daltons, or 500 daltons. In embodiments where two membranes are employed, they may have the same or different molecular weight cut-offs.

Materials employed in suitable membranes include for example: polysiloxane, polyurethane, polystyrene, poly(tetrafluoroethylene), cellulose, methyl cellulose, ethyl cellulose, and regenerated cellulose, poly(vinyl chloride), poly(vinyl flouride), poly(vinyl diflouride), poly(vinyl triflouride), and combinations and copolymers thereof.

In some embodiments, the volume enclosed by the sample channel is less than about 50 microliters, more preferably less than about 10 microliters, and still more preferably less than about 1 microliter.

In some embodiments, the means for applying the electrical field includes a pair of electrodes connected to a source of electrical potential, each positioned so as to be in electrically-conductive contact with the respective liquids. Accordingly, in embodiments where a single membrane is employed, one electrode is positioned within the first flushing channel such that it contacts flushing liquid when present, and the other is positioned within the sample channel such that it contacts the analytical stream when present; or, where two membranes are employed, the electrodes are positioned each within one of the flushing channels. In some embodiments, the solid material forming the flushing channel walls is an electrically conductive material; in other embodiments, the solid material forming the walls of the channels is a dielectric material, and the electrode may be a plate suspended within the channel or, more preferably, may be applied as an electrically-conductive layer onto a wall of the channel.

In some embodiments, the potential across the electrodes is at least about 100 mV, more usually at least about 1 V and still more usually at least about 10 V; and as high as about 1 kV, usually no higher than about 500 V, and still more usually no higher than about 200 V; the potential is most usually operated in the range about 10 V to about 200 V, at a current in the range of about 1 mA to about 100 mA, more usually in the range of about 5 mA to about 10 mA.

Suitable dielectric materials for construction of the solid parts of the apparatus include organic polymers such as, for example, polyvinyl chloride ("PVC"), polyethylene, polypropylene, polystyrene, poly(tetra fluoroethylene) ("PTFE"), poly(etheretherketone) ("PEEK"), poly(butadiene), melamine, poly(phenol-formaldehyde) resin, and combinations and copolymers thereof.

In another general aspect, the invention features a method for in-line flow-through sample treatment, by providing an apparatus according to the invention; providing a flow of flushing liquid through the flushing channel (or through both flushing channels, where two membranes are employed); moving an analytical stream into and through the sample channel by way of the sample inlet; enriching the sample stream by applying an electrical potential across the flowing sample stream, resulting in removal of smaller charged particles across the membrane (or membranes); and moving the enriched sample stream out from the sample channel by way of the sample outlet. The analytical stream may be a fractionated stream resulting from a separation operation (for example, liquid chromatography), and the enriched sample stream resulting from treatment according to the invention may be recovered and subjected to analysis, or may be further enriched, either again by the method of the invention or by another enrichment or purification method such as, for example, liquid chromatography, capillary electrophoresis, mass spectrometry, and the like.

In embodiments, having two membranes, the apparatus consists of a sample channel, through which the analytical stream flows, having dialysis membranes on two usually opposing sides and means to apply an electrical potential across both membranes. Positively- and negatively-charged molecules below the molecular weight cut-offs of the respective membranes are drawn through the membranes into the flushing liquid in the flushing channels and are thereby removed from the flowing sample stream, resulting in desalting of the sample stream and enrichment of the analytes in the stream.

In some such embodiments, the apparatus is a sandwich construction. At the center of the sandwich is an electrically insulating, generally flat flow channel plate having opposing surfaces and a peripheral edge, cut through to define two walls of a channel having a roughly rectangular section, an inlet and an outlet for a flowing sample. The dialysis membranes are laid onto the opposing surfaces of the channel plate so that they cover, and define the other two opposing walls of, the sample channel. Each membrane is held in place by an electrically insulating frame. One of the frames includes a sample inlet port and a sample outlet port, which are located in fluid-conducting relationship to the inlet and outlet, respectively, of the channel. Enclosed by each frame is an electrically conductive electrode plate, which is electrically connected to a source of electrical potential. Each electrode plate is cut away to provide an enclosed flushing channel over at least the portion of the membrane that covers and defines a wall of the channel, and has inlet and outlet ports communicating with the flushing channel for a flow of flushing fluid.

In some embodiments, the permeable membranes have a molecular weight cut-off of 30,000 daltons, preferably 10,000 daltons, more preferably 5,000 daltons, more preferably 1,000 daltons, and most preferably 500 daltons.

DETAILED DESCRIPTION OF THE INVENTION

Particular embodiments, will now be described in detail with reference to the drawings, in which like parts are referenced by like numerals. The drawings are not to scale and, in particular, certain of the dimensions may be exaggerated for clarity of presentation.

Figure 5A:
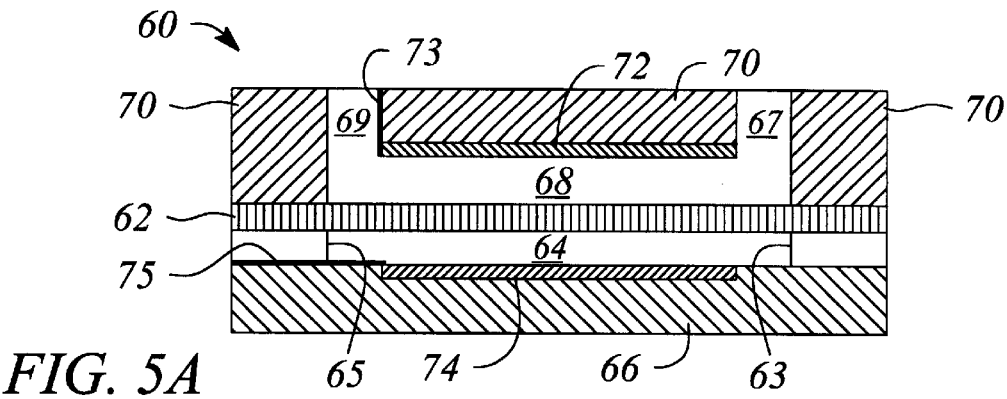
FIG. 5A is a diagrammatic sketch in a sectional view, lengthwise thru the sample channel, of an exemplary apparatus according to the invention, employing a single membrane.
Figure 5B:
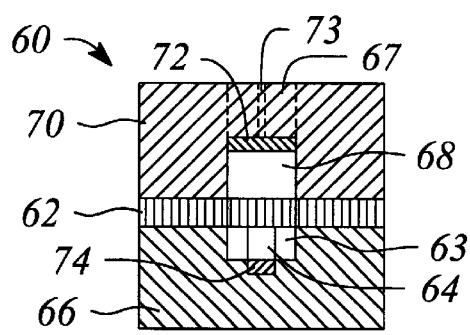
FIG. 5B is a diagrammatic sketch in a sectional view, transversely thru the sample channel, of the apparatus as in FIG. 5A.

Referring first now to FIGS. 5A, 5B, there is shown by way of example generally at 60 micro-dialysis apparatus according to the invention in which a single membrane is employed. The Figures are diagrammatic and in sectional view, the section in FIG. 5A being made lengthwise the sample channel, and the section in FIG. 5B being transverse the sample channel and midway its length. Membrane 62 is constrained between blocks 70 and 66 by mating surfaces of the blocks. Blocks 70 and 66 are constructed of a solid dielectric material (not necessarily the same material for both blocks), which may conveniently be a glass, ceramic, or a fused silica, for example, or a rigid organic polymer such as a PVC, a polyethylene, a polypropylene, a polystyrene, a poly(butadiene), a melamine, a poly(phenol-formaldehyde) resin, a PTFE, or a PEEK, or the like, or some combination or copolymer. Walls of sample channel 64 are formed as an open trench or groove in block 66, and sample inlet 65 and sample outlet 63 are formed as bores in block 66. A part of membrane 62 covers the trench, so that the sample channel is defined between sample inlet 65 and sample outlet 63 in part by the walls of the trench in the solid block and in part by one surface of the portion of membrane 62 that covers it. Similarly, walls of flushing channel 68 are formed as an open trench or groove in block 70, and flushing liquid inlet and outlet 67, 69 are formed as bores in block 70; and a part of membrane 62 covers the trench, so that the flushing channel is defined in part by the walls of the trench in solid block 70 and in part by the other surface of the portion of membrane 62 that covers it. Sample inlet 65 is provided with a conventional fluid connector leading from an upstream source of sample stream, which may be, for example, a separation device (not shown in the Figures) such as, for example, a chromatography column. And sample outlet 63 is provided with a conventional fluid connector leading to apparatus (not shown in the Figures) for recovering, for further treating (for example, for further enrichment or separation), or for analysis of the enriched sample stream. Flushing fluid inlet and outlet 69, 67 are provided with conventional fluid connectors leading from a source of flushing fluid and to a repository or drain for dialysate.

One electrically conductive member 72 of an electrode pair is affixed to a wall of flushing channel 68 away from membrane 62, and the other electrically conductive member 74 of the electrode pair is affixed to a wall of sample channel 64. The electrically conductive members 72, 74 are electrically connected to an external source of electrical potential (not shown in the Figures) by connectors 73, 75, respectively.

Figure 6A:
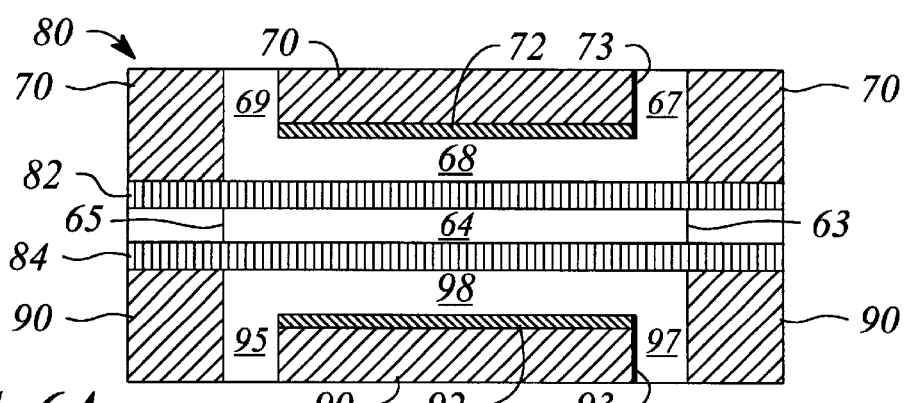
FIG. 6A is a diagrammatic sketch in a sectional view, lengthwise thru the sample channel, of an exemplary apparatus according to the invention, employing two membranes.
Figure 6B:
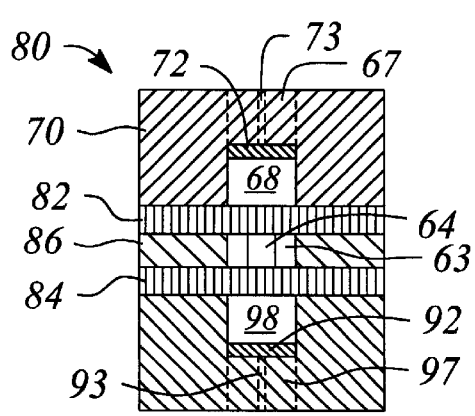
FIG. 6B is a diagrammatic sketch in a sectional view, transversely thru the sample channel, of the apparatus as in FIG. 6A.

Referring now to FIGS. 6A, 6B, there is shown by way of example generally at 80 micro-dialysis apparatus according to the invention in which two membranes are employed. The Figures are diagrammatic and in sectional view, the section in FIG. 6A being made lengthwise the sample channel, and the section in FIG. 6B being transverse the sample channel and midway its length. Membrane 82 is constrained between block 70 and channel block 86, and membrane 84 is constrained between block 90 and channel block 86 by mating surfaces of the blocks. Blocks 70 and 90 and channel block 86 are constructed of a solid dielectric material (not necessarily the same material for all the blocks), which may conveniently be a glass or a fused silica, for example, or a rigid organic polymer such as a PVC, a polyethylene, a polypropylene, a polystyrene, a PTFE, or a PEEK, or the like, or some combination or copolymer, as listed above. Walls of sample channel 64 are formed as a slot formed through channel block 86, and sample inlet 65 and sample outlet 63 are formed as lengthwise bores or as extensions communicating with the slot in block 90. A part of membrane 82 covers the slot on one side, and a part of membrane 84 covers the slot on the other side, so that the sample channel is defined between sample inlet 65 and sample outlet 63 in part by the walls of the slot in the solid channel block and in part by one surface of the portion of each of membranes 82 and 84 that cover the slot on opposite sides. Walls of flushing channel 68 are formed as an open trench or groove in block 70, and flushing liquid inlet and outlet 67, 69 are formed as bores in block 70; and a part of membrane 82 covers the trench, so that the flushing channel is defined in part by the walls of the trench in solid block 70 and in part by the other surface of the portion of membrane 82 that covers it. Similarly, walls of flushing channel 98 are formed as an open trench or groove in block 90, and flushing liquid inlet and outlet 97, 95 are formed as bores in block 90; and a part of membrane 84 covers the trench, so that the flushing channel is defined in part by the walls of the trench in solid block 90 and in part by the other surface of the portion of membrane 84 that covers it. The membranes 82, 84, as well as the membrane 62 of FIGS. 5A and 5B, are made from electrically insulating polymers that are independently selected from the membrane materials listed above. The sample inlet and outlet 65, 63 and the flushing fluid inlets and outlets 67, 69, 97, 95 are provided with conventional fluid connectors and are connected to other apparatus (not shown in the Figures) generally as described above with reference to FIGS. 5A, 5B.

One electrically conductive member 72 of an electrode pair is affixed to a wall of flushing channel 68 away from membrane 82, and the other electrically conductive member 92 of the electrode pair is affixed to a wall of flushing channel 98. The electrically conductive members 72, 92 are electrically connected to an external source of electrical potential (not shown in the Figures) by connectors 73, 93, respectively.

In use, a flow of flushing liquid flows through the flushing channel (or through both flushing channels, where two membranes are employed). An analytical stream is directed into the sample channel by way of the sample inlet, through the sample channel, and out from the sample channel by way of the sample outlet. The analytical stream may be a fractionated stream resulting from a separation operation (for example, liquid chromatography). An electrical potential is applied across the flowing sample stream, resulting in removal of smaller charged particles across the membrane (or membranes) as the sample stream flows through the sample channel. The enriched sample stream resulting from treatment may be recovered and subjected to analysis, or may be further enriched, either again by treatment in the apparatus according to the invention or by another enrichment or purification method such as, for example, liquid chromatography, capillary electrophoresis, mass spectrometry, and the like.

The voltage applied across the electrodes will be selected according to the particular configuration and dimensions of the channels, by applying principles known in the electrodialysis art. Generally, the electric field hastens and may otherwise enhance the dialysis process. As a result, a satisfactory enrichment can result from a shorter retention time in the sample channel, and this can have the desirable effect of reducing dispersion effects. A higher potential may be expected within limits generally to produce a more rapid dialysis. However, if the field is too strong, charged particles that are above the nominal cut-off for the membrane may be forced against the membrane, or an excessive current may result in unacceptable heating of the sample stream and degradation of analyte components. Accordingly, the strength of the electric field will be kept within a range high enough to provide a beneficial enhancement of the dialysis and a beneficial shortening of the residence time, without adversely affecting the sample fractions in the sample stream.

Figure 1:
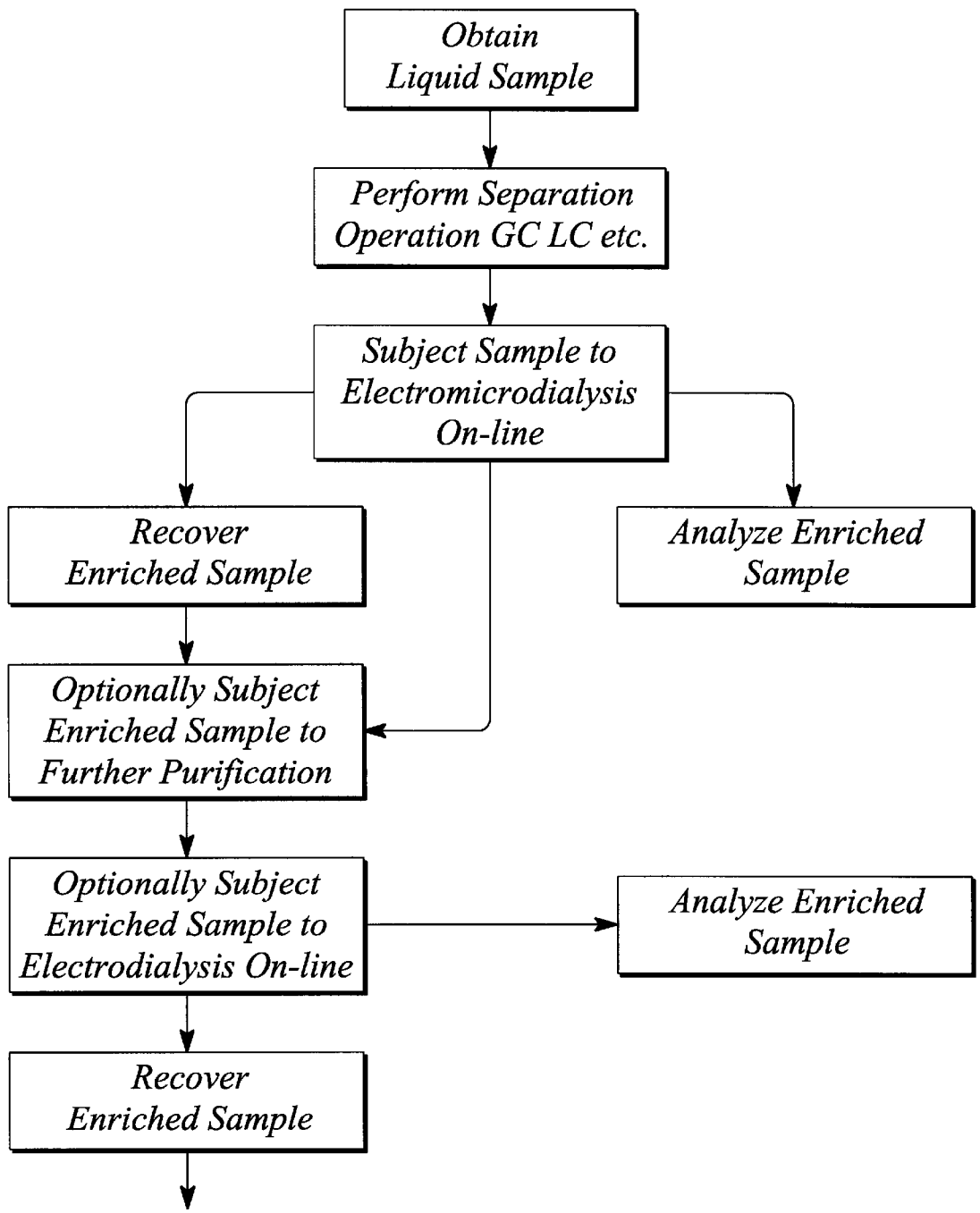
FIG. 1 is a schematic flow diagram showing a continuous on-line process employing the method according to the invention.

Referring now to FIG. 1, there is shown a flow diagram illustrating an embodiment of the method of the invention. In an on-line continuous system, a separation device, such as a liquid chromatograph or a gas chromatograph, is used to provide fractions of an obtained crude liquid analyte mixture of components. This crude liquid analyte mixture is channeled in a micro-volume, flow-through, electro-dialysis device consisting of a flow channel with dialysis membranes on two sides and means for establishing an electrical potential through the liquid across both membranes such that both positive and negative molecules below the molecular weight cutoff of each membrane are drawn through the membranes into the dialysate and removed from the flowing on-line sample. The enriched sample may be recovered or optionally subjected to further fractionation and/or enrichment as needed. Alternatively, the enriched sample may be analyzed directly.

For analytes of interest, positively charge molecules, negatively charged molecules and neutral molecules can be removed from the flowing analyte in solution. A judicious choice of molecular weight and cut-off for the permeable membrane with the application of an electrical potential, is useful to remove undesired materials and to enrich the desired analyte within the flowing sample within an acceptable time period.

The combination of microdialysis and an electrical field reduces the time required to remove the charged molecules (salts) from the flowing sample. This removal thus reduces the volume of the flow path required or specific residence time and consequently reduces the extra column band broadening.

Figure 2:
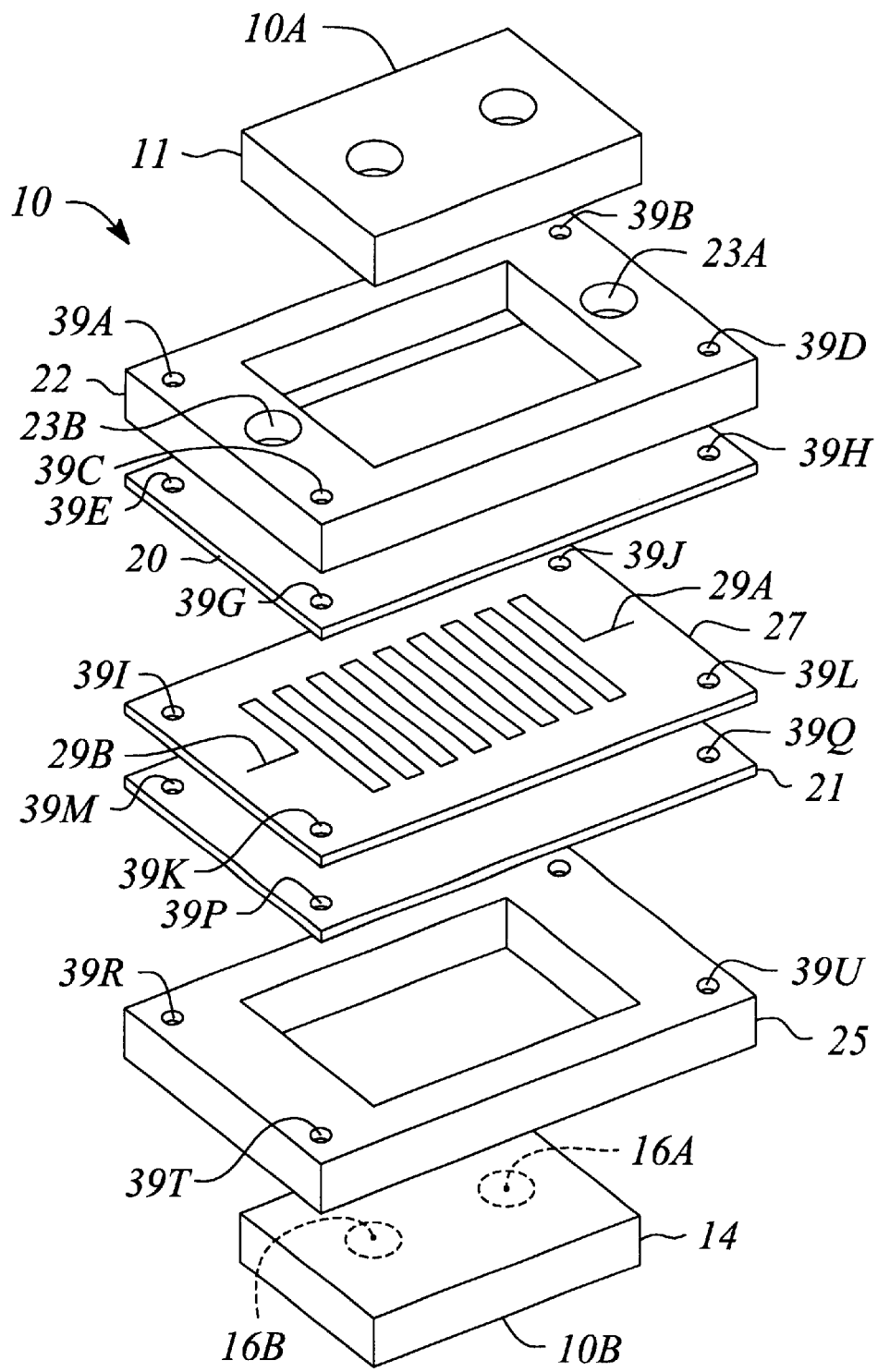
FIG. 2 is an exploded schematic isometric representation of an embodiment of an on-line electromicrodialysis device according to the invention.

With reference to FIGS. 2, 3A–3G, and 4, a particular embodiment of the apparatus of the invention, and of its use in the method of the invention, are described. FIG. 2 is an exploded schematic isometric view of the device 10. Positive first electrode plate 11 has two (cylindrical) openings 12A outlet and 12B inlet which narrow down (conically) to outlet port 13A and inlet port 13B (also see FIG. 3A). Similarly, negative second electrode plate 14 has two openings (cylindrical) 15A inlet and 15B outlet which narrow down conically to inlet port 16A and outlet port 16B (also see FIG. 3C). These electrode plates are electrically conducting. Contacts 10A and 10B are connected to a source of electrical potential (not shown) to complete the electrical circuit.

Each plate contains a relatively large volume for pumping dialysate in space 17A and 17B across surface 18 and surface 19 of membrane 20 and 21, respectively as illustrated in FIGS. 3B, 3F, 3C, and 3E, respectively.

First sample support plate 22 is generally rectangular in shape having a central opening for positive electrode plate 11 to fit within. Support plate 22 also includes openings (cylindrical) 23A and 23B for the introduction of a sample, which narrow conically to inlet port 24A and outlet port 24B as further illustrated in FIG. 3B.

Figure 3A:
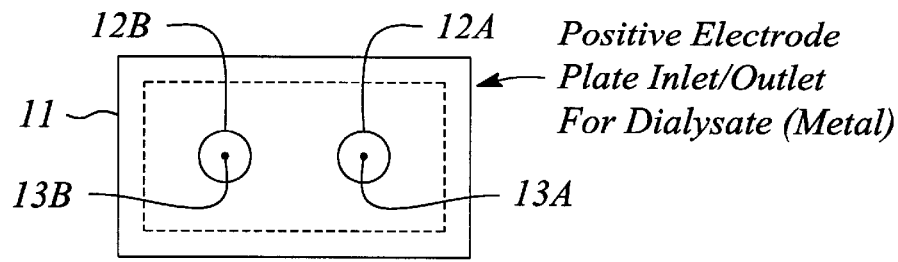
FIGS. 3A to 3G are schematic representations in plan view of components of the on-line electromicrodialysis device of FIG. 2.
Figure 3B:
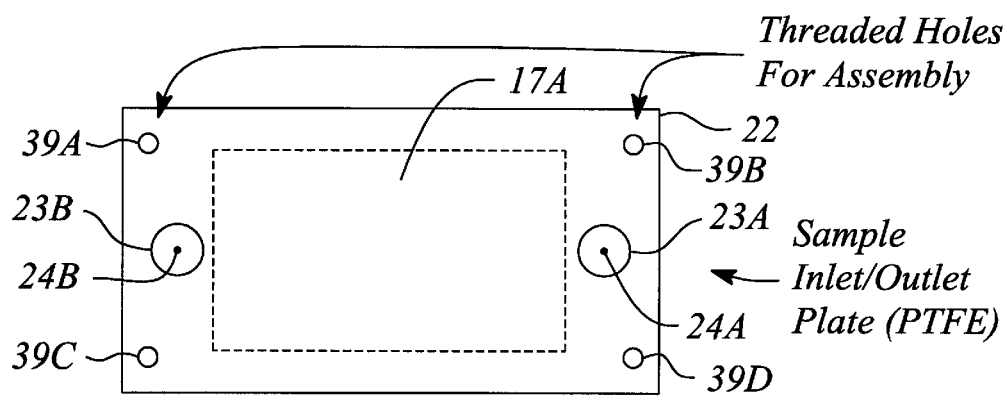
Figure 3C:
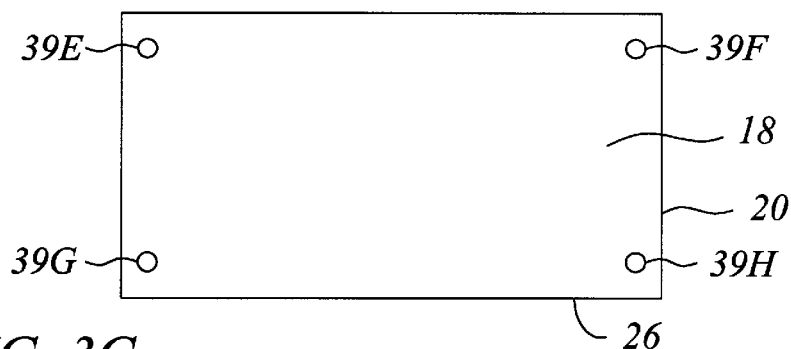
Figure 3D:
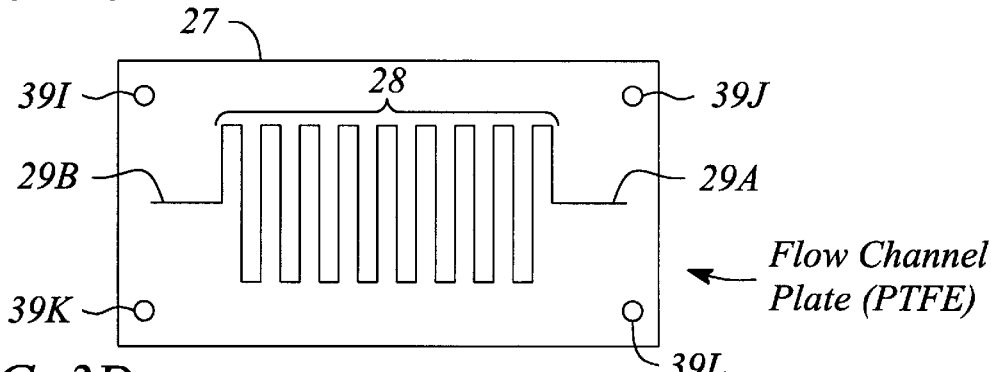
Figure 3E:
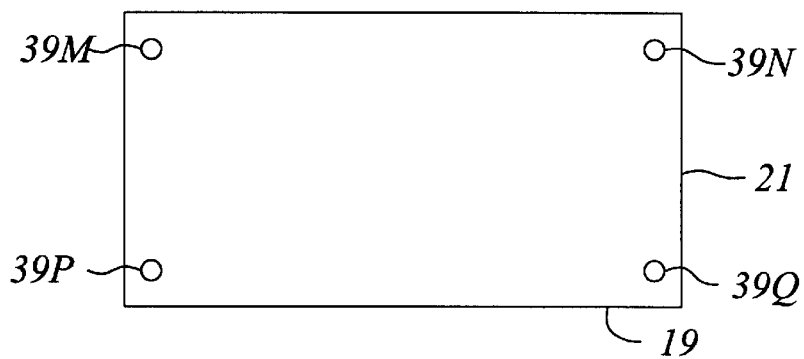
Figure 3F:
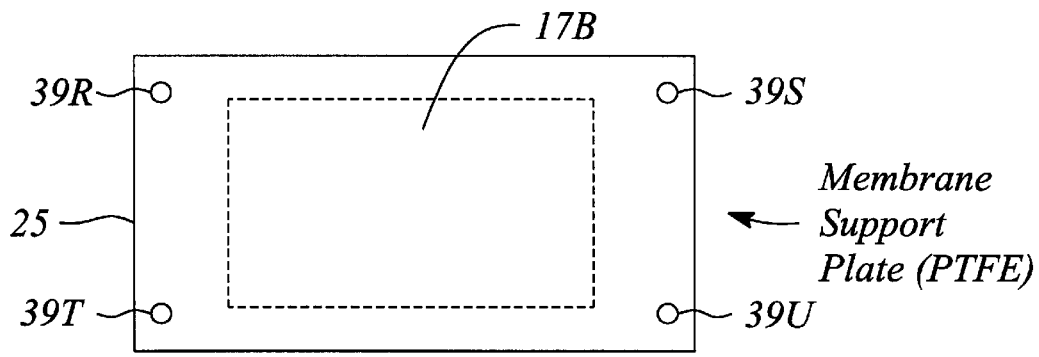
Figure 3G:
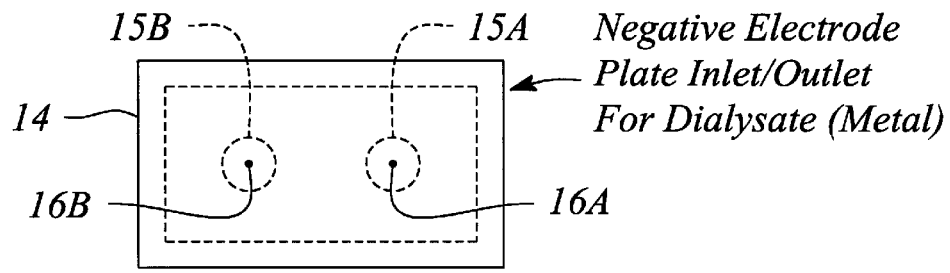

Similarly, second electrically insulating membrane support plate 25 is generally rectangular having a central opening for negative electrode place 14 to fit within (also see FIG. 3F). Support plate 25 does not have openings for a sample as found in support plate 22.

A surface 26 of permselective membrane 20 contacts a surface of the electrically insulating flow channel plate 27. Channel plate 27 has a channel 28 and inlet port 29A and exit port 29B, as further illustrated in FIG. 3D.

The openings 39A to 39N and 39P to 39U identify those openings used to screw the device together to produce functioning liquid tight compartments in the device.

Figure 4:
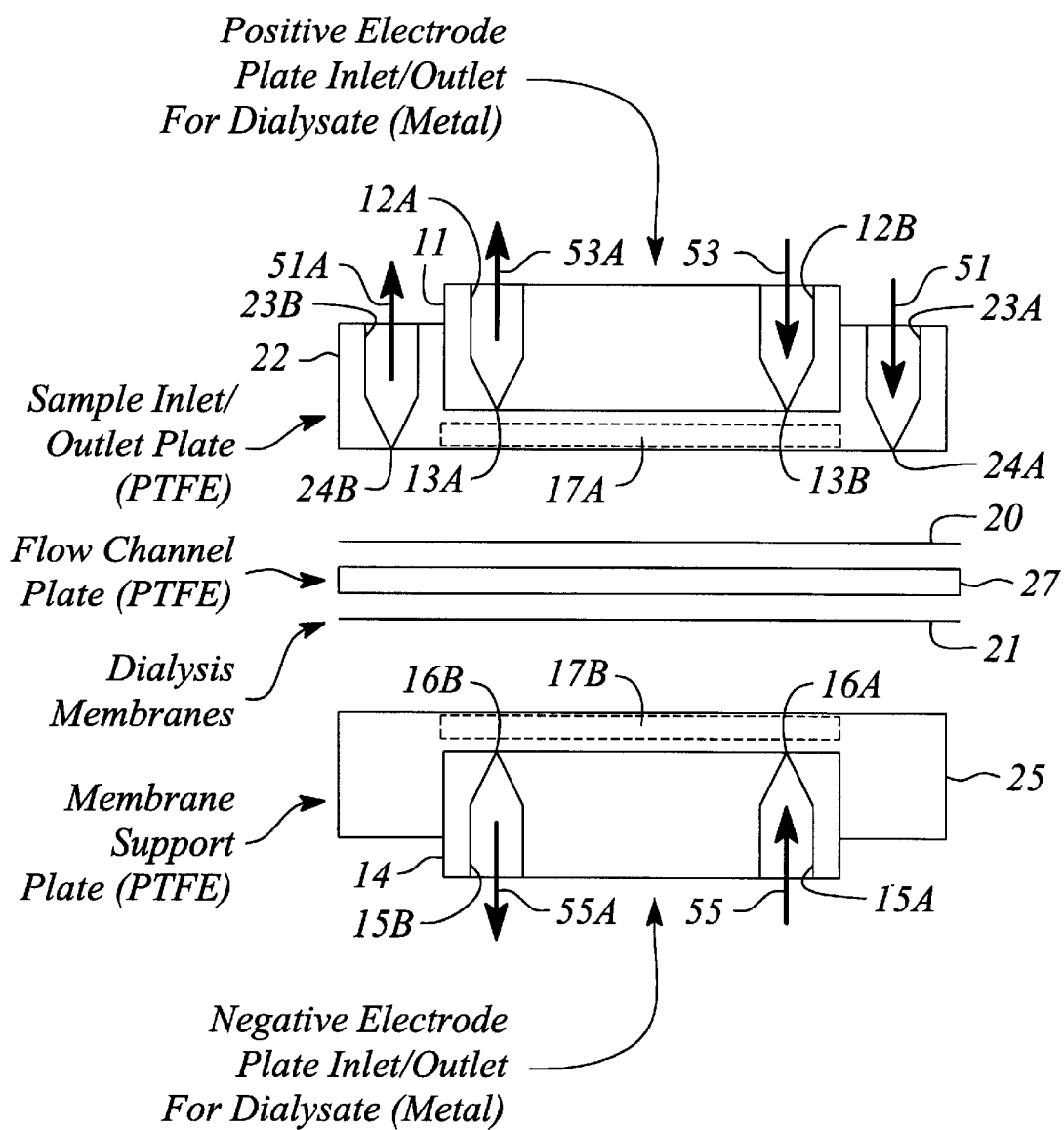
FIG. 4 is a schematic representation of a sectional view of the assembled on-line electromicrodialysis device of FIG. 2.

With regard to FIG. 4, the enrichment of a liquid sample containing at least one uncharged organic analyte, a positively charged molecule and a negatively charged molecule is illustrated. A crude sample 51 enters inlet 23A passes through inlet port 24A of support plate 22 and into inlet port 29A of flow channel plate 27 (inlet port 29A is illustrated in FIG. 2 with respect to flow channel plate 27), passes through channel 28, exits flow channel plate 27 as sample 51A via outlet port 29B (again refer to FIG. 2 for outlet port 29B) and passes through outlet 23B of support plate 22 via outlet port 24B thereof. The darkened arrows labeled 51 and 51A illustrate the path of the crude sample 51 in FIG. 4.

While passing through channel 28 the sample is in contact with membrane 20 and membrane 21 and is subjected to an electrical potential through the dialysate 53, 55. The dialysate 53 enters inlet 12B passes through inlet port 13B into reservoir space 17A in contact with surface 18 of membrane 20 and exits as dialysate 53A. Similarly, dialysate 55 enters inlet 15A passes through inlet port 16A into reservoir space 17B in contact with surface 19 of membrane 21, and exits as dialysate 55A via outlet port 16B and through outlet 15B. The darkened arrows labeled 53, 53A, 55, 55A illustrate the paths of dialysates 53, 55 in FIG. 4.

Under the influence of the electrical potential, the smaller negatively charged molecules in the sample 51 permeate through membrane 20 into the dialysate in reservoir 17A. On the other hand, the smaller positively charged molecules permeate through membrane 21 into the dialysate in reservoir 17B. The enriched sample (now reduced in positively charged molecules and negatively charged molecules, i.e., salts) in channel 28 is recovered or subjected to further treatment.

Although the Figures show some possible constructions, the invention is not limited to this approach or these materials. The two electrode plates must be made of an electrically conductive material. Each contains a relatively large volume for pumping dialysate across the membrane surface. Since the sample does not pass through this volume, it can be as large as is easy to construct. The electrode plates fit into upper an lower membrane support plates which are constructed of a non-conductive material. One of these contains fittings for attaching the inlet from the HPLC (or other upstream separation or purification apparatus) and for attaching the outlet to analytical apparatus, such as for example, an ionization source for mass spectrometry. Low molecular weight cutoff dialysis membranes (e.g., 100–500 MWCO) are sandwiched between the membrane support plates and the flow channel plate. The flow channel plate is a thin piece of electrically non-conductive material (e.g., PTFE) which has a flow channel cut into it. The channel length and the plate thickness determine the channel volume and the residence time for a given flow rate. This channel should be as small as possible. Practically, it encloses a volume in the range less than several microliters, preferably in some embodiments, 1 microliter or less. The entire apparatus is held together with screws and housed in some type of electrically non-conductive housing to prevent electrical shock to the technician.

In practice, the salt and analyte-containing effluent from the LC is connected to the upper membrane support plate via a minimum length (and volume) of narrow internal diameter tubing. The salts and analytes enter the flow channel. The analyte molecules that are larger than the MW cutoff pass through the channel and exit the outlet with minimal extra-column dispersion and are then directed to the mass spectrometer (or other analytical apparatus). As the low molecular weight salts pass through the channel, they are drawn through the membrane to the appropriate electrode (anions to the positive anode, cations to the negative cathode) where they are swept away in the dialysate flow. This process would be significantly accelerated compared to simple dialysis where diffusion is the dominant force.

The application of an electrical field to on-line microdialysis apparatus according to the invention decreases the time required for removal of salts from the sample stream. By reducing this time, dispersion of analyte peaks is reduced, resulting in improved analytic fidelity. The apparatus is easy to use, requires only low maintenance, and carries a low cost.

EXAMPLES

The following examples are presented for the purpose of illustration and description only. They are not to be construed to be limiting in any way.

Example 1

This Example illustrates application of the invention for desalting the effluent from ion exchange chromatography prior to electrospray mass spectroscopy. In operating a high performance ion exchange chromatographic separation which is done for the separation of proteins and peptides, mobile phase constituents include varying amounts of phosphates, chlorides, sulfates, and the like, which are not compatible with electrospray ionization. By inserting the apparatus of the invention in-line between the exit of the ion exchange column and the inlet of the electrospray ion source, results can be obtained without compromising either system.

Example 2

This Example illustrates application of the invention for removal of trifluoroacetic acid ("TFA") from reversed phase separations prior to electrospray mass spectrometry. Peptide mapping is conventionally done using 0.1–05% trifluoroacetic acid ("TFA") as a mobile phase. TFA causes substantial reduction of ion abundance in electrospray ionization mass spectrometry. By inserting the apparatus of the invention in-line between the exit of the ion exchange column and the inlet of the electrospray ion source, results can be obtained without compromising either system.

Example 3

This Example illustrates application of the invention for desalting HPLC effluent prior to capillary electrophoresis ("CE"). The mobile buffers and components (including organic solvent) used in HPLC interface with separation processes in capillary electrophoresis. To couple HPLC with CE in a multidimensional heart-cutting procedure, the device of this invention of FIG. 2 is used to desalt the HPLC effluent prior to transfer to the CE.

Example 4

This Example illustrates application of the invention for separation of a recombinant protein using ion exchange chromatography and electrospray ionization mass spectrometry. Ion exchange separation of a recombinant protein is coupled with Electrospray Ionization Mass Spectroscopy ("ESI-MS"). The separation is conducted on a Synchropak CM300 column using a mobile phase gradient of 0.01 M sodium phosphate (pH 6.0) to 0.01 M sodium phosphate in 0.5 M sodium chloride in 30 min. at a flow rate of 1.0 ml/min. In this case the sodium phosphate and sodium chloride are not compatible with ESI-MS, but are removed by running the column effluent through the microelectrodialysis unit having membranes with 10,000 MW cutoff and applying 100 to 200V to dialyze the salt components out of the solvent.

Example 5

This Example illustrates application of the invention for removal of TFA from a sample stream. A reversed phase separation of proteins is conducted using a VYDAC C4 column with a mobile phase gradient from 0.1% TFA, 20% acetonitrile to 0.1% TFA, 60% acetonitrile in 30 min. at a flow rate of 0.2 ml/min. TFA present in the mobile phase can cause a substantial reduction of ion abundance in subsequent ESI treatment. Conducting the column effluent through the microelectrodialyzer with a 10,000 MW cutoff membrane and applying 100 to 200 V, the TFA is removed prior to ESI-MS analysis.

Example 6

This Example illustrates application of the invention for desalting an HPLC effluent. This example is performed in the manner described in Example 1 with the following modifications. Instead of introducing the column directly into the electrospray ionization mass spectrometer, a valving arrangement is set up such that during the elution of a specific peak, a small volume is automatically introduced into the capillary electrophoresis and re-concentrated using transient isotachophoresis.

While only a few embodiments, of the invention have been shown and described herein, it will become apparent to those skilled in the art that various modifications and changes can be made in the method and apparatus for on-line flow through micro-dialysis for concentrating a sample and improving dispersion without departing from the spirit and scope of the present invention. All such modifications and changes coming within the scope of the appended claims are intended to be carried out thereby.

What is claimed is:

1. Apparatus for in-line flow-through sample treatment, comprising a sample channel having a length and opposite ends, a sample inlet located at one end and a sample outlet located at the opposite end, and the sample channel being defined in a first surface of a first block of solid material, such that the sample channel is enclosed along its length in part by inner surfaces of walls of the first solid material except at the first surface of the first material where the sample channel is enclosed by an inner surface of a first membrane, and a first flushing channel having a length and opposite first ends, an inlet port located at one first end and an outlet port located at the opposite first end, and the first flushing channel being defined in a surface of a second block of solid material, such that the first flushing channel is enclosed along its length in part by inner surfaces of walls of the second solid material except at the surface of the second material where the first flushing channel is enclosed by an outer surface of the first membrane, and means for applying an electric field across the first membrane in liquids carried within the sample channel and the first flushing channel.

2. Apparatus of claim 1 wherein the sample channel is further defined through the first block of solid material to a second surface of the first block located opposite to the first surface, and the sample channel is further enclosed along its length by an inner surface of a second membrane at the second surface of the first material, and wherein the apparatus further comprises a second flushing channel having a length and second opposite ends, an inlet port located at one second end and an outlet port located at the opposite second end, and the second flushing channel being defined in a surface of a third block of solid material, such that the second flushing channel is enclosed along its length in part by inner surfaces of walls of the third solid material except at the surface of the third material where the second flushing channel is enclosed by an outer surface of the second membrane, and wherein the means for applying an electric field comprises means for applying the electrical field across both the first membrane and the second membrane in liquids carried within the sample channel and the flushing channels.

3. Apparatus for on-line electromicrodialysis for desalting of a liquid sample to enrich an analyte therein before or after liquid chromatography or capillary electrophoresis, which apparatus comprises:

a first positive electrically conducting electrode plate, which includes an inlet port and an outlet port for dialysate, which plate is in contact with a first electrically insulating membrane support plate including a sample inlet port and a sample outlet port, which support plate is in contact with a first electrically insulating dialysis membrane in contact with a center electrically insulating flow channel plate having a channel, an inlet port and an outlet port for a sample, a second electrically insulating dialysis membrane in contact with a second electrically insulating membrane support plate, which is in contact with a second negative electrically conducting electrode plate, which plate includes an inlet port and an outlet port for dialysate.

4. Apparatus of claim 3 wherein the first and second electrically insulating dialysis membranes have a molecular weight cut-off of about 30,000 daltons.

5. Apparatus of claim 3 wherein the first and second electrically insulating dialysis membranes have a molecular weight cut-off of about 1,000 daltons.

6. Apparatus of claim 3 wherein the channel has a volume of about 50 microliter.

7. Apparatus of claim 3 wherein the first and second electrically insulating membranes have a molecular weight cut-off of 1,000 daltons, and the channel has a volume of about 1 microliter.

8. Apparatus of claim 3 wherein the first electrically insulating membrane support plate, the center electrically insulating flow channel plate, and the second electrically insulating membrane support plate are made from materials independently selected from the group consisting of glass, ceramic, and organic polymer, wherein the organic polymer is selected from the group consisting of polyethylene, polypropylene, poly(butadiene), poly(vinyl chloride), melamine, poly(phenol-formaldehyde) resin, polystyrene, and poly(etherether ketone), and combinations and copolymers thereof.

9. Apparatus of claim 8 wherein the first and second electrically insulating membranes have a molecular weight cut-off of 1000 daltons, and the channel has a volume of about 1 microliter or less.

10. Apparatus of claim 3 wherein the first electrically insulating dialysis membrane, and the second electrically insulating dialysis membrane are independently selected from the group consisting of poly(vinyl chloride), poly(vinyl fluoride), poly(vinyl difluoride), poly(vinyl trifluoride), poly(tetrafluoroethylene), and poly(siloxane), and combinations and copolymers thereof.

11. Apparatus of claim 10 wherein the first and second electrically insulating membranes have a molecular weight cut-off of 1000 daltons, and the channel has a volume of about 1 microliter or less.

12. Apparatus of claim 3 wherein the electrical potential across the membrane is between about 0.1 micro volt and 100 micro volt and the current is between about 0.1 micro amp and 100 m amp.

13. A method for on-line electromicrodialysis for desalting of a liquid sample to enrich an analyte therein before or after liquid chromatography or capillary electrophoresis, which process comprises:

(a) providing apparatus according to claim 3, (b) contacting a sample with a liquid chromatography apparatus to separate components of the sample creating one or more fractions;

(c) contacting a fraction of step (b) with an apparatus component of step (a) with electrical bias being applied to the positive first electrically conducting electrode plate and to the negative second electrically conducting electrode plate which produces an enriched sample by removing electrically charged constituents of the fraction sample by electrodialysis; and (d) either
  (i) recovering the enriched sample, or
  (ii) subjecting the enriched sample to further purification, electromicrodialysis, or analysis.

14. The method of claim 13 wherein the first and second electrically insulating dialysis membranes have a molecular weight cut-off of about 30,000 daltons.

15. The method of claim 13 wherein the electrical potential between the first and second electrode plates is between about 0.1 microvolt and 100 m volt.

16. The method of claim 13 wherein the channel has a volume of about 50 microliters.

17. The method of claim 13 wherein the first and second electrically insulating dialysis membranes have a molecular weight cut-off of about 1,000 daltons, the electrical potential between the first and second electrode plates in between about 0.1 micro Volt and 100 m Volt; and the channel has a volume of about 50 microliters.

* * * * *